United States Patent [19]

Acosta et al.

[11] Patent Number: 5,550,146
[45] Date of Patent: Aug. 27, 1996

[54] MEDICAL FOODS FOR THE NUTRITIONAL SUPPORT OF INFANT/TODDLER METABOLIC DISEASES

[75] Inventors: Phyllis J. B. Acosta, Westerville; Richard A. Grondalski, Columbus; Jeffrey W. Liebrecht; Patricia A. Reynolds, both of Columbus, all of Ohio

[73] Assignee: Abbott Laboratories, Abbott Park, Ill.

[21] Appl. No.: 423,177

[22] Filed: Apr. 18, 1995

Related U.S. Application Data

[62] Division of Ser. No. 230,452, Apr. 20, 1994, which is a continuation of Ser. No. 997,278, Dec. 23, 1992, abandoned.

[51] Int. Cl.$^6$ .................... A61K 31/415; A61K 31/40; A61K 31/205; A61K 31/195
[52] U.S. Cl. .................... 514/400; 514/419; 514/423; 514/561; 514/562; 514/556; 514/565; 514/566; 514/578
[58] Field of Search .................... 424/601, 682, 424/646, 643, 630, 639, 667; 514/2, 23, 58, 549, 552, 558, 556, 561, 565, 566, 562, 400, 423, 419, 578; 426/2, 72, 73, 74, 658

[56] References Cited

U.S. PATENT DOCUMENTS

| 4,252,822 | 2/1981 | Berry | 424/319 |
|---|---|---|---|
| 4,340,592 | 7/1982 | Aditi | 424/177 |
| 5,034,377 | 7/1991 | Aditi | 514/18 |

FOREIGN PATENT DOCUMENTS

| 903028876 | 3/1990 | European Pat. Off. . |
|---|---|---|
| 891187421 | 4/1990 | European Pat. Off. . |
| 58-165742 | 9/1983 | Japan . |
| 58-180429 | 9/1983 | Japan . |
| 59-5111 | 1/1984 | Japan . |
| 59-53429 | 3/1984 | Japan . |
| 2038629 | 7/1990 | United Kingdom . |

OTHER PUBLICATIONS

Cow & Gate Medical Handbook 1990 Edition.
Scientific Hospital Supplies, Update, vol. 1, 1993.
Mead Johnson Special Metabolic Modules, Mead Johnson Product Handbook, 1993.
Dietary Management of Metabolic Disorders, Mead Johnson, 1993.
CRC Handbook of Chemistry and Physics, 57th Edition, (1976–1977), pp. D–216 and 217.
Martindale, The Extra Pharmacopeia, 28th Edition, (1982), p. 1691.
The Merck Index, 11th Edition, (1989) pp. 1433–1434.

*Primary Examiner*—Raymond Henley, III
*Attorney, Agent, or Firm*—L. R. Drayer; T. D. Brainard

[57] ABSTRACT

The present invention relates generally to a generic powder base rich in fats, carbohydrates, vitamins and minerals and trace elements which can be readily admixed with specific amino acids to yield several different therapeutic products for use in the nutritional support of various inherited metabolic diseases.

2 Claims, No Drawings

MEDICAL FOODS FOR THE NUTRITIONAL SUPPORT OF INFANT/TODDLER METABOLIC DISEASES

This application is a divisional of application Ser. No. 08/230,452 filed Apr. 20, 1994, which is a continuation of application Ser. No. 07/997,278 filed Dec. 23, 1992, now abandoned.

TECHNICAL FIELD

The present invention relates generally to a a novel generic powder base rich in fats, carbohydrates, vitamins, minerals and trace elements which can be readily admixed with specific amino acids to yield several different therapeutic products for use in nutritional support of various inherited metabolic diseases.

BACKGROUND OF TEE INVENTION

The present invention relates to novel nutritional products (medical foods) for the treatment of various inherited metabolic disorders and methods of manufacturing these medical foods. These products comprise different amino acid mixtures in combination and admixture with a common nutritional base of fats, carbohydrates, vitamins and minerals (hereinafter referred to as the "Premix Base") which supplies the specific nutritional and energy requirements of the patient. Each individual amino acid formulation is particular for the nutritional support of a specific metabolic disorder as discussed below.

Inborn errors of metabolism occur when there is a block in a pathway in a metabolic sequence. The block results in an accumulation of normal intermediary products in abnormally large amounts and also of products of usually little used metabolic pathways. In most instances this effect can be attributed to the accumulation of an intermediary product proximal to the block. The accumulated toxic effects of these intermediary metabolites can be treated by restricting the intake of the essential substance from which the toxic metabolite is derived. Sometimes, the block prevents the synthesis of an essential compound normally made distal to the block and therapy consists of specifically providing this metabolite.

Infants with certain inborn errors of amino acid or nitrogen metabolism can be treated with special diets that restrict one or more amino acids to the minimum amount essential for normal growth. The amount of the restricted amino acid provided by the diet must be sufficient to meet the metabolic requirements dependent on it, but it must not permit an excess accumulation in the body fluids of the amino acid or its derivatives, or of nitrogen.

The nutrient requirements can be met by providing a semisynthetic diet, derived either from a modified protein hydrolysate or from a mixture of L-amino acids devoid of, or low in, the offending amino acid(s). Other food sources in prescribed amounts furnish the implicated amino acid(s) in an amount sufficient to support normal growth, yet low enough to avoid toxicity. Requirements for other essential nutrients are met by the addition of minerals and vitamins to the specific amino acid mixture during manufacture.

Careful monitoring is essential during nutritional support. The total nutrient intake should be known and monitored to be certain that the person is receiving a nutritionally adequate diet both in terms of essential nutrients as well as total energy intake. The plasma concentration of the appropriate amino acid(s) or ammonia in disorders of the urea cycle should be determined frequently to assure that the level is adequate to sustain normal protein metabolism, but not high enough to be harmful.

Nutritionally balanced medical foods presently available provide adequate fat and carbohydrate, as well as essential protein, vitamins, and minerals. The total nutrient composition of the special dietary product is considered so that the product provides not only all of the amino acid requirements, except the implicated amino acids, but also trace minerals, vitamins, and other micronutrient requirements. For an infant, the special diet often also meets total energy needs. The requirement for the implicated amino acid may be derived from the addition of infant formula, or other selected foods in prescribed amounts. Conventional low protein foods are used as part of the diet for children after infancy.

Different types of products have been developed for use in diets of infants and of older persons with inborn errors of metabolism. Energy supplements can be combined with the appropriate amino acid mixtures, and limited conventional foods, for nutritional support under medical supervision.

For disorders of amino acid metabolism, products with specially treated protein hydrolysates or amino acid mixtures are used. All currently available commercial products require the addition of prescribed amounts of regular infant formula, milk, low protein or conventional foods.

From a historical perspective, essentially four types of medical foods are known. These may be summarized as follows:

Type 1 products contain levels of amino acids or protein, vitamins, and minerals appropriate for feeding infants with the exception of the amino acid(s) not metabolized by the patient.

Type 2 products contain somewhat higher levels of amino acids or protein, vitamins, and minerals to meet the needs of older subjects. However these products are all either devoid of or low in the amino acid(s) that cannot be metabolized by the patient.

Type 3 products include amino acid mixtures free of the amino acids which cannot be metabolized with complete vitamin and mineral supplements but with little or no added carbohydrate or fat.

Type 4 products consist of modules that require the addition of a special amino acid mixture for amino acid disorders, selected carbohydrates for disorders of carbohydrate metabolism or intolerance, or selected fat for disorders of fat metabolism or intolerance.

Whichever metabolic food is selected, it is done so with consideration for the patient's nutrient and energy needs. A person's actual dietary intake, growth and nutritional status, blood values for the implicated amino acid, and other tests for nutritional sufficiency are monitored periodically. Caution is needed when using special medical foods to treat disorders of amino acid metabolism because of the genetic individuality and particular nutrient needs of each patient. The preparation of specific diets from synthetic or semisynthetic products in combination with natural foods is best done by experienced people.

For older infants and children, in order to meet the total nutrient requirement, larger amounts of Type 1 medical foods must be consumed. This volume requirement may not allow sufficient flexibility in adding other foods to the diet. In such instances, Type 2 medical food that are higher in protein, vitamins, and minerals, or Type 3 amino acid mixtures are then useful, since smaller amounts are needed in the diet and this permits inclusion of more regular low protein foods in the diet.

Most of the early commercial products developed for the treatment of inborn errors of metabolism were of Type 1. These products were primarily amino acid mixtures or protein hydrolysates and often lacked some essential vitamins or minerals, which made preparation of nutritionally adequate and balanced diets difficult. This type of product typically required the addition of vitamins A, D, E, C, and K to make balanced diets for children and adults, and also required supplementation with choline, inositol, and some trace minerals to prepare formulas for infants. Type 4 medical foods include balanced modules with complete vitamin and mineral mixtures which are free of either protein (for amino acid disorders or protein intolerance), carbohydrate (for carbohydrate disorders or carbohydrate intolerance), and fat (for disorders of fat metabolism or fat intolerance).

Based on nutrient and energy requirements as a function of age, it is necessary to develop separate product lines for patients with the same inherited metabolic disorder but who fall into the infant/toddler versus child/adult category. Infant/toddler are classified as being less than four years of age and the child/adult is classified as being four or more years of age. This distinction Between the two groups is based on differences in nutrient and energy requirements as discussed below. Nutrient and energy requirements of the infant and toddler on a body weight basis are greater than for the child and adult, because of the rapid growth rate of the infant and toddler in comparison to that of the child. The adult has only maintenance, not growth, requirements for nutrients and energy. Thus, from a medical food perspective the infant/toddler-formula should have a high fat content to supply the energy needs whereas the child/adult formula should be lower in fat and higher in protein equivalent content in order to obviate weight gain concerns.

Examples of various disease conditions, resulting from inborn errors of metabolism, that can be clinically managed by nutritional support with the medical foods of the present invention are discussed individually and in detail below.

1. Phyenylketonuria (PKU)

The primary metabolic defect in PKU is the inability to convert excess dietary phenylalanine to tyrosine. As a result of this metabolic block, phenylalanine accumulates in the blood and cerebrospinal fluid and is excreted in excess in the urine. Abnormally high levels of phenylalanine are diverted to the formation of phenylpyruvic acid and its metabolic derivatives, phenylacetic, phenyllactic acid and orthohydroxyphenylacetic acids. There is excessive excretion in the urine of these acids. There is interference with the normal metabolism of tyrosine and tryptophan, and unusual intermediary products of these two amino acids appear in the urine.

Mental retardation, usually of a severe degree, is one of the clinical manifestations of this disease when left untreated. Petit and grand mal seizures occur frequently, and there also is a high incidence of abnormal electroencephalograms, even in the absence of convulsions. The neurologic manifestations in untreated patients include muscular hypertonicity, exaggerated tendon reflexes, tremors and hyperkinesis. In about 15–20% of the untreated cases a dermatitis resembling infantile eczema is reported. Many cases demonstrate disorders of pigment metabolism. The presence of phenylacetic acid in the urine and perspiration gives an odor described as musty, or similar to mouse excrement.

Nutritional support is used to limit the intake of phenylalanine, in order to avoid any excess accumulation of this amino acid. A certain minimum phenylalanine requirement individual to each affected child, however, must be provided in the diet in order to facilitate normal growth and tissue repair and to maintain the plasma phenylalanine level in the normal range. A phenylalanine intake of between 50–70 mg/kg/day is required for infants with PKU 2–4 months of age. The symptoms of insufficient phenylalanine intake include apathy, anorexia, hypoglycemia, and vacuolization of the marrow erythroid and myeloid cytoplasm. Death after prolonged hypoglycemia due to insufficient phenylalanine intake has been observed. The phenylalanine requirement in terms of body weight decreases rapidly during the first year of life. Readjustment of the phenylalanine intake must be made frequently during this year.

The effect of the restricted phenylalanine diet on mental development in PKU children is directly related to the age at which the diet is instituted. Children with PKU seem to develop normally if they receive a low phenylalanine diet beginning very soon after birth. The IQ of children with PKU fell linearly by about 4 IQ points for each month between birth and starting treatment, for each 300 umol/l rise above normal in the average plasma phenylalanine concentrations, and for each five months within the first two years or life during which the phenylalanine concentration were below 120 umol/l.

As mentioned above, treatment of PKU requires the dietary restriction of phenylalanine intake. All naturally occurring proteins contain approximately the same amount of phenylalanine (about 4–6% of total amino acids). Thus, it is not possible to provide enough protein for the growing child without exceeding the low phenylalanine requirement and which results in elevated plasma phenylalanine levels. This can result in dangerous excess accumulation of this amino acid. In order to overcome this problem, the nitrogenous moiety of the diet is provided in the form of a casein hydrolysate treated in such a manner that most but not all of the phenylalanine is removed. Alternatively a mixture of synthetic L-amino acids, which contains no phenylalanine, may be used as the dietary nitrogen and amino acid source. Tyrosine is an essential amino acid and since it is the distal metabolic product of phenylalanine conversion it is necessary in such dietary formulations to include sufficient tyrosine in the diet to meet nutritional requirements.

There are a number of reported clinical cases of mental and physical retardation occurring in the offspring of PKU mothers who were not receiving specific nutritional support for PKU at the time of conception and during their pregnancies. These offspring themselves do not have PKU. These children are damaged in utero by the high maternal levels of phenylalanine. Plasma phenylalanine levels of PKU mothers must be controlled during pregnancy. Treatment with a phenylalanine restricted diet during pregnancy, particularly if initiated before conception, appears to offer some protection to the fetus from birth defects. When the blood phenylalanine levels are well controlled during the entire pregnancy the infant seems to be normal.

Several medical foods are currently on the market for the nutritional support of patients with PKU. Among these is the product, Lofenalac™ manufactured by Mead Johnson Corporation, Evansville, Ind., U.S.A. Lofenalac™ contains approximately 0.08% phenylalanine and is produced from an enzymatic hydrolysate of casein. Phenylalanine is removed from the casein hydrolysate by adsorption on activated charcoal columns. This formula is supplemented with carbohydrates, fats, minerals, vitamins and L-tyrosine, L-tryptophan, L-methionine and L-histidine dihydrochloride. Three other casein hydrolysate-based products were developed in England: Albumaid XP™, Cymogran™, and Minafen™.

Albumaid XP™ (Powell and Scholefield, Ltd., England) is a bovine serum hydrolysate from which most of the phenylalanine is removed and which contains 40% protein equivalent along with some vitamins and minerals. For feeding patients, this product needs to be supplemented with fat, vitamin C, fat-soluble vitamins, and essential fatty acids.

Cymogran™ (Alan and Hanbury's Ltd., London, England) contains 30% protein equivalent along with moderate levels of fat and carbohydrate. It requires supplementation with all vitamins and some minerals, as well as some dilution with low-protein foods.

Minafen™ (Cow & Gate, Trowbridge, England), a balanced infant formula-type product, contains about 8% of the energy requirements, but as a low phenylalanine protein hydrolysate, it is deficient in several vitamins.

Another commercially available product for the nutritional support of PKU is PKAid 1™ (Powell and Scholefield, Ltd.) which is an amino acid mixture free of phenylalanine. The other amino acids are present in satisfactory amounts. This enables dietary supplementation to supply the minimum phenylalanine requirement. Supplementation with carbohydrate, fat, and all vitamins and minerals is necessary.

Phenyl-Free™ (Mead Johnson Corp., Evansville, Ind., U.S.A.), is another medical food used for the nutritional support of PKU. This product is a mixture of L-amino acids excluding phenylalanine. It contains vitamins, minerals, carbohydrates and a small amount of fat. When this product is reconstituted with water, one pint of the product provides 400 kcal and contains the daily requirements of vitamins, minerals and essential amino acids. For a child two years of age or older, the additional energy and phenylalanine requirements can be met from conventional low protein foods given in prescribed amounts. The product has the characteristic bitter taste of L-amino acid mixtures, but is palatable when flavored.

Other commercial available products for the control of PKU include PKU-1™, PKU-2™ and PKU-3™ (Milupa, Fredrichsdorf/Taunus, Germany) which comprise phenylalanine free amino acid mixtures, complete vitamin and mineral supplementation, and small amounts of sucrose designed for use in the diets of infants and older-age patients. These products supply respectively 70–80% of the energy as protein. Dilution with protein-free and low protein foods is necessary to prepare balanced formulas and diets. These prior art formulations are nutritionally incomplete in that they are devoid of fat and selenium. Other medical foods available for the nutritional support of PKU include Analog XP®, MaxamaidXP® and MaxamumXP®. These products, manufactured by Scientific Hospital Supplies, Liverpool, England, are all nutritionally incomplete dietary products.

2. Other Metabolic Disease Conditions Related To Either Phenylalanine or Tyrosine Abnormalities.

(a) Tyrosinemia Type 1

Tyrosinemia Type 1 is an inherited disorder of tyrosine metabolism, associated with deficient activity of fumarylacetoacetate hydrolase. Patients present with severe liver and renal disease in infancy and in later childhood develop hepatomas. Biochemically the disease is characterized by raised plasma levels of tyrosine and methionine and increased urinary excretion of tyrosine metabolites.

A diet low in tyrosine, phenylalanine, and often methionine has until recently been the only treatment for type 1 tyrosinemia. Such treatment does not appear to prevent the long term development of hepatic complications, and attention has focused on the recent success of liver transplantation. The diet must be administered until a matching liver for transplantation is located. These studies however preceded the identification of the enzyme defect and used plasma tyrosine and methionine, and urinary tyrosine metabolites to monitor dietary treatment effectiveness.

(b) Tyrosinemia Type II

Tyrosinemia Type II is associated with autosomal recessive inheritance and has distinctive metabolic abnormalities, including increased levels of tyrosine in the plasma and urine, and increased levels of tyrosine metabolites in the urine. The defect in oculocutaneous tyrosinemia is in the tyrosine aminotransferase of the hepatic Cytosol, an enzyme that normally catalyzes the conversion of tyrosine to p-hydroxyphenylpyruvic acid. Deficient enzyme activity results in tyrosine accumulation and blood tyrosine concentrations become elevated. This syndrome is often associated with a characteristic clinical syndrome of eye and skin lesions, permanent neurological damage, mental retardation, and blindness. Early diagnosis is of paramount importance for effective treatment of the disorder.

Treatment typically consists of a low-tyrosine, low-phenylalanine diet. One such commercially available diet is the Mead Johnson Low Phe/Tyr Diet Powder™ (Mead Johnson Corp., Evansville, Ind., U.S.A.). This product is generated from a casein hydrolysate with most of the tyrosine removed while still containing substantial phenylalanine. Rapid decreases of tyrosine plasma levels have been reported in response to restriction of the dietary intake of phenylalanine and tyrosine. Symptoms have been observed to respond quickly to changes in the concentration of tyrosine in body. Other commercially available products for the treatment of tyrosemia include TYR-1™ and TYR-2™ (Milupa, Fredrichsdorf/Taunus, Germany) which are similar in composition to PKU-1™ and PKU-2™ (Milupa, Fredrichsdorf/Taunus, Germany) but which are devoid of both tyrosine and phenylalanine. Both products are used for the nutritional support of tyrosinemia and contain complete vitamin and mineral mixtures and small amounts of sucrose. The products must be diluted with low-protein and protein-free foods, and fat must be added for feeding to infants and children. Other medical foods available for the nutritional support of tyrosinemia include Analog XPhen, Tyr, Met; Analog XPhen, Tyr and Maxamaid XPhen, Tyr all of which are manufactured by Scientific Hospital Supplies (Liverpool, England). These products are nutritionally incomplete and typically require supplementatation with at least two of the following: selenium, fat or carbohydrate.

(c) Alcaptonuria

The symptoms of alcaptonuria first appear in adult life in the form of a discoloration in the connective tissue (ochronosis) and a characteristic arthritis transmitted as an autosomal recessive absence of homogentisic oxidase, which results in excretion of homogentisic acid in the urine. A diet low in phenylalanine and tyrosine should reduce the formation of homogentisic acid, but there have not been any reported attempts with this therapy; however, a restriction of protein intake might have some beneficial effect.

3. Maple Syrup Urine Disease (MSUD) is another inborn error of metabolism that the medical food of the instant invention is designed to treat. These infants appear normal at birth, but after a few days they develop a poor appetite, become apathetic and lethargic, and then manifest neurologic signs, such as loss of normal reflexes. Alternating periods of atonia and hypertonicity appear, followed by convulsions and respiratory irregularities. MSUD is most often accompanied by a characteristic odor in the urine, perspiration and ear wax. The odor has been described as sweet, caramel-like or malty. If this disease is left untreated it is almost always fatal in the first weeks of life. These children are extremely sensitive to any condition which causes tissue breakdown, such as infection, fever, or fractures.

The classical form of MSUD involves almost complete deficiency of branched-chain keto acid dehydrogenase complex. The metabolic event that causes MSUD is a failure of the oxidative decarboxylation of the branched chain amino acids, leucine, isoleucine and valine. As a consequence, the keto acid derivatives accumulate in excess in the blood and are excreted in the urine. There is also an accumulation of the branched chain amino acids. Alloisoleucine also appears, as a result of the enolization of the alpha-keto beta methylvalerate.

MSUD can be treated with a diet providing a limited intake of the branched chain amino acids. Following nutritional support as indicated, the characteristic MSUD odor disappears, neurologic manifestations gradually improve, the electroencephalogram returns to normal, and the abnormal plasma accumulation of the branched chain amino acids and their keto acid derivatives decreases.

Initial treatment normally requires the use of a diet completely devoid of leucine, isoleucine, and valine, in order to reduce the plasma levels as rapidly as possible. Supplementation is begun as the plasma levels of these amino acids approach normal values. Usually valine and isoleucine become normal several days before the leucine level is in the normal range. After biochemical control is achieved, the intake of the branched chain amino acids can be provided in the form of prescribed amounts of infant formula, milk or low protein foods.

Commercial products available for the treatment of MSUD include MSUD-Aid™ (Powell and Scholefield, Ltd., England) which is a mixture of crystalline L-amino acids devoid of the branched-chain amino acids. This is a powdered product that contains minerals and water soluble vitamins. Fat soluble vitamins and additional calories from carbohydrate and fat are needed to meet general nutritional requirements; additional protein is needed as a minimal source for the branched-chain amino acids. Other medical foods available for the treatment of MSUD include MSUD Diet Powder™ (Mead Johnson Corporation), MSUD-1™, MSUD-2™ (Milupa), Analog™, Maxamaid™ and Maxamtun MSUD™ (Scientific Hospital Supplies). Since these prior art formulations are generally free of fat and selenium and low in carbohydrate content, patients ingesting these products typically require nutritional supplementation.

Classic branched chain ketoaciduria (BCKA) causes severe neurologic damage, a failure to grow and early death. This is an inborn error of metabolism resulting from the absence or inactivity of the branched chain keto acid dehydrogenase. The defect hampers the metabolism of the three-branched chain amino acids: leucine, isoleucine, and valine. As a consequence, these amino acids and their respective alpha-keto acids accumulate in the blood and in other body fluids. Plasma BCKA concentrations can be stabilized satisfactorily by restricting dietary protein intake and supplementing the diet with an amino acid mixture free of BCKA.

4. Isovaleric Acidemia.

Isovaleric acidemia is an inherited defect of leucine metabolism characterized by the presence of high levels of isovaleric acid (IVA) in the blood and urine. IVA is a short chain fatty acid whose only known amino acid precursor is leucine. In this condition the activity of isovaleryl CoA-dehydrogenase, the enzyme for IVA degradation, is deficient and is the enzyme defect in this disorder. The metabolic block is the failure to convert isovaleryl-CoA to beta-methylcrotonyl-CoA resulting in the large accumulation of IVA and metabolites, isovalerylglycine and beta-hydroxyisovaleric acid, in blood and urine. Even in remission these metabolites are present in increased quantities.

Clinically this condition is accompanied by an odor very similar to that of sweaty feet. Bouts of vomiting, lethargy, acidosis, and coma usually occur as a consequence of infection or increased protein intake. Brain damage resulting in mental retardation and other neurologic sequelae has also been reported. The site of the metabolic block is such that the usual screening procedures for detecting an amino acidopathy will not detect the disease. The presence of the unusual odor might lead one to suspect the presence of isovaleric acidemia.

Since IVA seems to be solely derived from leucine, which is an essential amino acid, reduction in dietary leucine is effective in controlling the abnormal accumulation of metabolites as well as sequelae.

Further, since glycine conjugation with isovaleryl-CoA dehydrogenase is instrumental in preventing IVA accumulation, it is advisable to restrict substances which compete for glycine conjugation, such as benzoic and salicylic acids. The administration of glycine favors the formation of non-toxic isovalerylglycine (IVG) from precursor IVA and hence the consequent diminution of toxic levels of IVA in blood and tissue. Glycine therapy is particularly beneficial for the treatment of acute ketoacidotic episodes in older infants and children, and for the management of acute neonatal disease. Glycine markedly reduces the rise in serum IVA produced by a leucine load. Glycine administration is associated with a pronounced increase in excretion of IVG and in hippurate excretion—both IVG and hippurate excretion being increased significantly by glycine administration as compared with administration of leucine alone.

Furthermore in isovaleric acidemia, when adequate carnitine is available, a new metabolite, isovalerylcarnitine (IVC), is excreted in large amounts. The use of carnitine therapy in isovaleric acidemia appears to be as effective as glycine therapy in the removal of isovaleryl-CoA and is more effective in reducing plasma IVA. IVC formation is not enhanced by glycine supplementation, and renal loss does not appear to account for the initially diminished levels of free carnitine.

5. Homocystinuria

The basic metabolic defect in homocystinuria is a deficiency in the activity of the enzyme cystathionine synthetase which catalyzes an essential step in the trans-sulferation pathway associated with cystine synthesis. Typically this enzyme deficiency results in abnormal levels of homocystine in the urine.

About half of the diagnosed cases of homocystinuria are associated with mental retardation. Other important clinical symptoms include: ectopia lentis (dislocated lenses), and a number of skeletal deformities. Arterial and venous thromboses are frequent occurrences and are responsible for sudden death. These effects are secondary to the damage caused to the blood vessel walls by homocystine. Therapy should be attempted in all cases of homocystinuria in an effort to avoid the serious pathological sequlae described above.

There are at least two types of homocystinuria caused by cystathione synthetase deficiency. One form is amenable to therapy with large doses of pyroxidine, at least several hundred milligrams per day. The other form requires a diet restricted in methionine and supplemented with cystine.

Both biochemical and clinical responses have been reported with diets low in methionine. These diets must be supplemented with cystine, since the site of the metabolic block makes cystine a dietary essential for these individuals.

Several products are available commercially for the nutritional support of homocystinuria. Since soy protein is low in methionine, soy protein isolate has been used to prepare a low-methionine infant formula, Low Methionine Diet Powder™ (Mead Johnson Corp., Evansville, Ind., U.S.A.). A similar product line, Low-MET Isomil™ (Ross Laboratories, Columbus, Ohio, U.S.A.), was also introduced but has since been discontinued. Methionaid™ (Scientific Hospital Supplies Ltd., Liverpool, England) is a methionine-free synthetic mixture of L-amino acids, water soluble vitamins, fat soluble vitamins and minerals. High-fat and carbohydrate foods must be added as well as several vitamins and some minerals in order to provide a complete diet. Milupa (Fredrichsdorf/Taunus, Germany) has recently introduced HOM-1™ and HOM-2™ which also provide methionine-free mixtures of amino acids, which contain mixtures of vitamins and minerals but no fat and little carbohydrate. Other medical foods available for the nutritional support of this disorder include Analog, Maxamaid and Maxamum XMet all of which are produced by Scientific Hospital Supplies. Since these prior art formulations are generally free of fat and selenium and low in carbohydrate content, patients ingesting these products typically require nutritional supplementation in order to provide an adequate and appropriate energy supply for the individual. Further, the Milupa products utilise an insoluble form of cystine which the body cannot adequately adsorb.

6. Urea Cycle Disorders.

Interruptions in the metabolic pathway for urea synthesis are caused by the deficiency or inactivity of any one of several enzymes involved in specific steps in the cascade. The common pathologic sequlae of these clinical disorders is the extreme elevation of the plasma ammonia level. Typically associated with this increase in ammonia buildup are acute episodes of vomiting, lethargy, convulsions and abnormal liver enzyme levels. Protracted exposure to high levels of plasma ammonia leads to mental and physical retardation. If left untreated prolonged exposure to high levels of plasma ammonia is fatal typically following a period of lethargy, convulsions and coma.

Several enzyme deficiencies have been noted as contributing to urea cycle disorders. These include:

(a) N-acetyl glutamate synthetase deficiency causes neurologic deterioration due to elevated blood ammonia.

(b) Carbamyl phosphate synthetase (CPS) deficiency which is often a lethal disease with death occurring in the first weeks of life.

(c) Ornithine transcarbamylase deficiency (OTD) which is inherited in a sex-linked dominant manner and is generally fatal in the newborn male.

(d) Argininosuccinic acid synthetase which typically results in severe neurological impairment leading to mental retardation or death.

(e) Argininosuccinate lyase deficiencies result in clinical manifestations of retardation, spasticity, and episodes of convulsions. Plasma ammonia level are greatly elevated.

(f) Arginase deficiency results in severe neurologic deterioration over time. Plasma arginine concentrations are greatly elevated.

All of these disorders respond to some degree to restriction of protein intake. Acute episodes are usually precipitated by an increased protein intake, an infection or any incident that leads to a negative nitrogen balance. These acute episodes are best handled by the omission of protein and intravenous fluid therapy. Prolonged treatment of children by limiting protein intake to the minimal requirement together with adequate energy intake and supplements of essential amino acids has resulted in control of the plasma ammonia levels and alleviation of the clinical symptoms.

No single panacea is available and nutritional support is specific to the individual disorder. For example, in the case of CPS and OTD deficiencies dietary supplementation with arginine may be effective treatment for reducing plasma ammonia levels. Arginine is considered to be an essential amino acid in this disturbance because of the site of the metabolic block. Milupa (Fredrichsdorf/Taunus, Germany) has recently introduced UCD-1™ and UCD-2™ for the nutritional management of urea cycle disorders. These prior art formulations are nutritionally incomplete mixtures of vitamins and minerals containing no fat or selenium and little carbohydrate.

7. Organic Acid Metabolic Disorders.

The disorders of propionate metabolism, methylmalonic acidemia (MMA) and propionic acidemia (PA), are the most common disorders of organic acid metabolism in man. These disorders usually present in the neonatal period or early infancy with vomiting, lethargy and metabolic acidosis, which may progress to coma and death. The mainstay of treatment of PA and MMA is a diet restricted in isoleucine, methionine, threonine and valine. An inadequate isoleucine, methionine, threonine and valine intake leads to poor growth with chronic malnutrition, a serious complication of the organic acidemias.

(a) Propionic Acidemia (PA).

Deficiency or inactivity of propionyl-coenzyme A carboxylase results in the accumulation of propionyl-coenzyme A. Clinically, patients present with vomiting, dehydration, lethargy and hypotonia in early infancy and are found to have ketonuria and metabolic acidosis.

Normal dietary protein is toxic to these patients; toxicity is caused by the presence of excess metabolites of the the amino acids: isoleucine, methionine, threonine and valine. Infants with this disorder respond well to dietary restrictions of isoleucine, methionine, threonine and valine particularly in the presence of adequate energy and protein equivalent.

(b) Methylmalonicacidemia (MMA).

Methylmalonic acid accumulates as a result of inactivity of one of two enzymes sites: methylmalonyl-coenzyme A mutase or 5' deoxyadenosyl-B12 conversion. As with PA, patients with MMA generally present with vomiting, dehydration, lethargy and hypotonia in early infancy and are found to have ketonuria and metabolic acidosis.

In about half of the patients this metabolic defect has responded to the administration of large amounts of vitamin B12. The B12 responsive type is due to a defect in the metabolism of 5' deoxyadenosyl-B12, while the B12 nonresponsive type is the result of an alteration in the methylmalonyl-coenzyme A mutase.

Treatment of the nonresponsive form consists of restricting isoleucine, methionine, threonine and valine intakes and alkali therapy for the episodes of acidosis. Typically nutritional support requires severe limitation of the recognized propionate precursor amino acids: isoleucine, valine, methionine and threonine. Clinical response to nutritional support however is less significant than in PA and patients continue to accumulate and excrete large quantities of methylmalonic and propionic acid. This less satisfactory response is largely due to the continued catabolism of odd-chain fatty acids, cholesterol and bacterial fermentation in the gut which are recognized as sources of propionate, and catabolism of thymine as a source of methylmalonate accumulation.

(c) Glutaric Aciduria Type 1 (GA-1).

GA-1 is caused by a deficiency in the activity of glutaryl-coA dehydrogenase resulting in an accumulation of glutaryl-CoA and its hydrolysis product glutaric acid which is toxic. Glutaryl-coA is an intermediate in the catabolic pathways of lysine, hydroxylysine and tryptophan. Patients typically present with elevated plasma and urine concentrations of L-glutaric acid and there is a marked increase in the concentrations of lactic acid, isobutyric acid, isovaleric acid and alpha-methylbutyric acid in the urine.

GA-1 usually presents in infancy or early childhood with progressive neurological deficits including acute dysarthria, dystonia and choreoathetosis. In the absence of treatment, further bouts of encephalopathic crises lead to progressive motor deterioration accompanied by an increasingly severe generalized cerebral atrophy, most striking in the frontal and temporal lobes, and finally death. Typically the disorder arises from the near total absence or very low activity of the enzyme in liver, fibroblasts, and leukocytes. The disorder is inherited as an autosomal recessive trait and the enzyme deficiency results in plasma and cerebospinal fluid accumulation of glutaric acid and its principle metabolites 3-OH-glutaric acid, and glutaconic acid.

Therapeutic approaches for the control of GA-1 include long term nutritional support using diets low in tryptophan and lysine. Riboflavin, a co-enzyme for glutaryl CoA dehydrogenase, has been given to enhance residual enzyme activity. Large doses of L-carnitine has been used to stimulate excretion of short chain acylcarnitine derivatives of glutaric acid.

Medical foods available for the nutritional support of organic acid metabolic disorders include the Analog, Maxamaid and Maxamum products all of which are produced by Scientific Hospital Supplies. Since these prior art formulations are generally free of fat and selenium and low in carbohydrate content, patients ingesting these products typically require nutritional supplementation in order to provide an adequate and appropriate energy supply for the individual.

The above discussion indicates that numerous metabolic disease states exist for which the most appropriate therapeutic treatment is intervention through dietary management. Typically this involves ingestion of currently available commercial medical foods comprised of specific amino acid compositions. However several difficulties are associated with this clinical approach to management of the aforementioned metabolic disorders. Several of these problems are discussed below. As disclosed, the instant invention solves some of the problems associated with restricted diets.

Specifically incorporated herein, by reference for the purposes of further establishing the background of the present invention, are the following Patents and Patent Applications.

Japanese Patent No. Sho 58-165742 published Sep. 30th, 1983 and entitled *Nutrient Formula for Infants* discloses a highly digestible and adsorbable low protein nutrient formula for the nutritional support of urea cycle disorders. The formula comprises a low protein content combined with carbohydrates, fats, vitamins and minerals. The protein source is casein, whey proteins and synthetic amino acids. This prior art formulation differs from the instant invention in that it does not use a single or generic protein free powder Premix Base to supply the necessary nutritional and energy needs of the individual. The disclosed invention contains protein using casein and whey proteins as the principal amino acid source.

Japanese Patent No. Sho 59-5111 published Sep. 30th, 1983 and entitled *Nutrient Formula for Infants with Phenylketonuria* discloses an easily digestible, adsorbed and administered nutrient formula for the nutritional support of infants with Phenylketonuria. The nitrogen source is low in phenylalanine. This prior art formulation differs from the instant invention in that it does not utilize a generic powder Premix Base to supply the necessary nutritional and energy needs of the individual, and further in that it is not protein free since it uses hydrolyzed albumin as the amino acid source.

Japanese Patent No. Sho 59-53429 published Sep. 30th, 1983 and entitled *Nutrient Formula for Infants with Maple Syrup Urine Disease* discloses a nutrient formula for the nutritional support of Maple Syrup urine Disease. The formula comprises a leucine-, isoleucine- and valine-free nitrogenous source combined with fats, carbohydrates, minerals and vitamins. The source of the nitrogenous material is hydrolyzed albumin. This prior art formulation differs from the instant invention that it does not contain a common or generic protein free powder Premix Base to supply the necessary nutritional and energy needs of the individual and further in that it uses hydrolyzed albumin as the amino acid source.

Japanese Patent No. Sho 58-180429 published Sep. 30th, 1983 and entitled *Nutrient Formula for Infants with Homocystinuria* discloses use of nutrient formula for the nutritional support of Homocystinuria. The formula comprises a low methionine content protein source combined with carbohydrates, fats, vitamins and minerals. The source of the amino acids is either natural or partially hydrolyzed soy bean protein. This prior art formulation differs from the instant invention in that it does not contain a common or generic protein free powder Premix Base to supply the necessary nutritional and energy needs of the individual and further in that it uses natural or partially hydrolyzed soy bean protein as the amino acid source, requires cystine and tryptophan supplementation.

European Patent Application No. 90302887.6 filed Mar. 16th, 1990 and entitled *Dietary Product* discloses a nutrient formula for individuals requiring special dietary provisions. The formula comprises carbohydrates, fats and flavoring and specific amino acid supplementation. In particular, this prior art publication specifically addresses nutritional support of phenylketonuria. This prior art formulation differs from the instant invention in that it does not utilize a common or generic protein free powder Premix Base to supply the necessary nutritional and energy needs of the individual.

U.S. Pat. No. 4,252,822 issued Feb. 24th, 1981 and entitled *Method for Treating Phenylketonuria* discloses administration of a valine-isoleucine-leucine amino acid supplement mixture to a patient on a restricted phenylalanine diet. This prior art formulation differs from the instant invention in that it does not utilize a common or generic protein free powder Premix Base to supply the necessary nutritional and energy needs of the individual. Further, this prior art formulation contains only valine, isoleucine and leucine and as such is deficient in the other amino acids.

U.S. Pat. No. 4,340,592 issued Jul. 20, 1092 and entitled *Nutrient Compositions & Methods of Administering Same* discloses a nutrient composition comprised of di- and tri-peptides each having as the amino terminal residue the amino acid, glycine. These peptides can be combined with fats, carbohydrates, minerals and vitamins. This prior art formulation differs from the the instant invention in that it does not use a common or generic protein free powder Premix Base to supply the necessary nutritional and energy needs of the individual and further in that the instant application does not use glycine capped di-and tri-peptides.

U.S. Pat. No. 5,034,377 issued Jul. 23, 1991 and entitled *Aqueous Nutrient Compositions Comprising Oligopeptides* discloses use of at least two oligopeptides, one of which has glycine and the other having one of the following amino acids in the amino terminal position: alanine, arginine or lysine. Mixtures of these oligopeptides can be combined with fats, carbohydrates, minerals and vitamins. This prior art formulation differs from the instant invention in that it does not use a common-or generic protein free powder Premix Base to supply the necessary nutritional and energy needs of the individual and further in that the instant invention does not utilize oligopeptides.

UK Patent Application No. 2038629 published Jul. 30, 1990 and entitled *Dietary Compositions* relates to the development of a product regime wherein the necessary amino acids are provided as two separate components: one incorporating the more palatable amino acids, and the other comprising the more unpalatable amino acids in an amount of no more than about 20% by weight of the total. This results in the taste of the more unpalatable amino acids being masked or disguised thereby improving patient compliance. Specific amino acid compositions can be formulated, thereby allowing for the possibility of nutritional support of various metabolic disorders. This prior art formulation differs from the instant invention in that does not utilize a common or generic protein free powder Premix Base to supply the necessary nutritional and energy needs of the individual.

European Patent Application No. 891187421.1 published Apr. 18, 1990 and entitled *Proteinaceous Composition* discloses an edible composition designed to make palatable nutritional or other materials, such as pharmaceutical compositions or specific amino acid mixtures, which have an unacceptable taste. This is achieved by developing compositions, which can be formulated as confectionery snacks, comprising dried or candied fruit, a gelling agent, a flavor and the unpalatable material. This prior art composition differs from the instant invention in that it does not use a common or generic protein free powder Premix Base to supply the necessary nutritional and energy needs of the individual.

DISCLOSURE OF THE INVENTION

The present invention relates to a special high fat water soluble protein- and amino acid-free medical food powder (hereinafter referred to as a "Premix Base") consisting of oils, carbohydrates, minerals, vitamins, trace elements and antioxidants. The high fat water soluble Premix Base of the instant invention comprises by weight of dry powder, 31–39% fat and 60–68% carbohydrate, and wherein the percentage composition is defined on a dry weight basis as the number of grams of individual component per 100 grams of dry premix base powder. For example, 31–39% fat indicates that 31–39 grams of fat are contained in 100 grams of dry Premix Base powder and 60–68% carbohydrate corresponds to a content of 60–68 grams carbohydrate per 100 grams of Premix Base.

The high fat content in the range of 31–39% fat is what is considered critical. At this point in time, the specific oils forming the fat source are less important than the high fat content. In part this is because the medical foods of the instant invention are not the only nutrient source ingested by the patient for whom the products are intended. Said fat is selected from the group of oils consisting of pork lard, beef tallow, herring, menhaden, pilchard, sardine, babassu, castor, coconut, corn cottonseed, jojoba, linseed, oiticica, olive, palm, palm kernel, peanut, rice bran, rapeseed, safflower, sesame, soy, sunflower, tall and tung oils. In a preferred embodiment said fat comprises (a) at least one fat selected from the group consisting of palm oil and safflower oil, (b) coconut oil, and (c) soy oil, and wherein the ratio of palm (safflower):coconut:soy oils is in the range of 9:8:3 to 3:8:9 parts by weight.

To those skilled in the art of this invention, it will be clear that the fat content instead of being described on the basis of individual oil name can also be described in terms of fatty acid compositions, wherein said fatty acids are themselves constituents of the individual oils, and wherein said fatty acid components are characterized on the basis of carbon chain length, number and position of the double bonds (if any) present in the molecule, and wherein the chain length considered ranges from two (C2) to twenty-four (C24) carbon atoms.

The Premix Base serves a dual purpose: First, it can be employed as a protein-free, carbohydrate-fat-vitamin-mineral rich module for infants and toddlers who need extra calories and protein restriction in their diets. Examples of diseases/disorders in which the Premix Base is beneficial include those conditions in which the following corrective action is desirable:

(a) Modification of amino acid intake (eg. Hypervalinemia, Cystinuria, Ketothiolase deficiency, etc);

(b) Modification of protein intake (eg. Allergies, Hyperornithinemia-Homocitrullinuria-Hyperammonemia, Nonketotic Hyperglycinemia, etc);

(c) Modification of Energy, Vitamin, Mineral Intake (eg. Failure to thrive, Gastrointestinal problems such as Celiac disease, Crohns disease, Lactose intolerance, etc); and (d) Hypermetabolic states (eg. Burns, Cancer, Sepsis, Trauma, Movement Disorders (Choreic), etc.

Second, the Premix Base of the instant invention also serves as a generic base for admixture with certain amino acids in the modular formation of different medical foods for the nutritional support of specific metabolic disorders. Each individual amino acid formulation being particular for the nutritional support of a specific metabolic disorder. The amino acids used in this manner are the alpha amino acids which are known in the art as those amino acids from which mammalian proteins are comprised. Specifically excluded from the alpha amino acid group are carnitine and taurine.

More specifically, there is disclosed herein a generic protein-free Premix Base which is rich in fats, vitamins, carbohydrates, minerals and trace elements for use as the nutritional foundation to which various specific amino acid formulations may be added thereby forming unique compositions, generally referred to as medical foods, for use in the treatment of different metabolic disorders and wherein the fat content, ranging from 31–39% by weight, is derived from a combination of (a) palm and/or safflower, (b) coconut and (c) soy oils which are used in a ratio ranging from 9:8:3 to 3:8:9. Additionally methods for preparing the defined medical foods are disclosed herein.

The present invention further discloses several methods for overcoming the various problems previously encountered in nutritional support of metabolic disorders. One of the main problems related to the use of the prior art medical foods in the nutritional support of metabolic disorders is reduced patient compliance. That is to say, a failure of the patient to consume the nutritional product according to the recommended regimen. This is due to the lack of palatability of the presently available amino acid preparations. Typically this problem arises from the inclusion of amino acids in the nutrient mixes which have unacceptable taste or smell (organoleptic) characteristics. Examples of such unpalatable amino acids are aspartic and glutamic acid. Typically in the art this problem is overcome through the addition of specific agents which mask the unacceptable characteristics. Such agents include sugars and flavors. However while inclusion of such agents in medical foods achieves the goal of masking the organoleptically unacceptable characteristics their inclusion causes other potential problems for the patients. These problems include the possibility of allergic reactions to the additives and taste ennui.

Another problem with the currently available commercial products is that it is typically necessary to ingest a large volume of the product in order to supply the energy needed by the patient. The medical foods of the instant invention overcome this problem by employing a special fat blend in the range of 31–39% by weight of the Premix Base. This special fat blend allows a greater amount of energy to be supplied by a smaller volume of the medical food. This factor also helps with a patient's dietary compliance since it is now possible for the patient to consume less volume and still obtain proper nutrition.

A third problem with the current commercially available medical foods is that they are not cost-effective since they are manufactured in small quantities owing to the small market size associated with each specific metabolic disorder, which requires a specific formulation for each disorder. The medical foods of the instant invention are more cost-effective since they utilize a common premix powder base (Premix Base) consisting of fats/oils, carbohydrates, vitamins, minerals and various trace elements which is then dry blended with a specific amino acid formulation thereby yielding the desired therapeutic product. Cost effectiveness of the manufacturing process is improved since the Premix Base can be manufactured on a large scale and used as the base for each of the individual disease specific medical foods.

An additional problem with the current commercially available prior art dietary products is the lack of solubility of L-cystine. Owing to this lack of solubility, a substantial overload of L-cystine is typically added to the products in order to ensure that the minimum cystine requirements are provided. This strategy suffers however from not only the consequent inability to strictly control cystine intake but also from the attendent increase in cost required for enhanced cystine levels. The medical foods of the instant invention which specify cystine supplementation utilize cystine dihydrochloride (2.0–13.5 g/Kg of Premix Base product) to ensure the bioavailability of the L-cystine. As a result of this increased solubility, less L-cystine need be added to the medical food in order to ensure minimum requirements are met. Clearly this also translates into more cost effective and nutritious products.

Another problem encountered with the current commercially available prior art medical foods involves the inadequate amounts or complete absence of L-carnitine. Consequently for some metabolic disorders where large amounts of L-carnitine must be administered daily, the L-carnitine must be purchased and administered separately. This may cause problems because, since it is a separate item, there is a significant chance that it might be omitted and not administered. The medical foods of the instant invention incorporate L-carnitine directly in the Premix Base so that ingestion of L-carnitine is ensured. In certain selected products additional fortification with L-carnitine occurs at the time of dry blending of the Premix Base and the specific amino acid(s) mixture so that adequate ingestion of L-carnitine is ensured. Carnitine fortification is particularly required in the nutritional support of the urea cycle disorders and gyrate atrophy, leucine catabolic disorders including isovaleric acidemia and organic acid metabolic disorders including glutaric aciduria, propionic acidemia and methymalonicacidemia.

BEST MODE FOR CARRYING-OUT THE INVENTION

The Premix Base according to this invention serves a dual function: First, it can be employed as an amino acid and protein-free vitamin-mineral module for infants and toddlers who need extra calories and protein restriction in their diets. Second, the Premix Base according to this invention also serves as an amino acid and protein free, fat-carbohydrate-vitamin-mineral rich generic base for admixture with certain amino acids in the modular formation of different medical foods for the nutritional support of specific metabolic disorders. Another advantage of this invention includes the substantial increase in cost-effectiveness since the Premix Base can be prepared on a large commercial scale.

The present invention will now be explained on the basis of some specific embodying examples, which, however, are not to be considered as limiting. Unless otherwise noted "parts" are parts by weight.

EXAMPLE 1

Preparation of the Premix Base

Several individual steps are involved in the production of the amino acid and protein free Premix Base. For clarity the major steps are summarized below:
(1) Preparation of Stock Solutions:
 (a) Preparation of a water soluble vitamin mixture;
 (b) Preparation of an ascorbic acid mixture;
 (c) Preparation of oil blend containing oil soluble vitamins; and
 (d) Preparation of a carbohydrate/mineral slurry.
(2) Combination in a specified sequence of the Stock Solutions:
 (a) Combining the oil blend and carbohydrate/mineral slurry;
 (b) Addition of the water soluble vitamins to the slurry; and
 (c) Addition of ascorbic acid to the slurry.
(3) Drying the combined stock solutions to yield a powder Premix Base.
(4) Dry blending of the powder Premix Base with defined amino acid mixtures to yield various nutrient formulas for treating specific metabolic disorders (Example 2).

An example of the exact mass of each component used in the production of 1000 lbs (453.6 kG) of a final dry Premix Base according to a preferred embodiment is presented in Table 1.

TABLE 1

Constituents of the Premix Basw Infant/Todler Base Powder[1].

| Ingredient | Quantity per 1000 lbs | |
|---|---|---|
| | lbs | grams |
| WATER | 1084.0 | 491,692.0 |
| WATER SOLUBLE VITAMIN/MINERAL/TAURIN PREMIX | | |
| (a) Potassium Citrate | 0.032 | 14.68 |

TABLE 1-continued

Constituents of the Premix Basw Infant/Todler Base Powder[1].

| Ingredient | Quantity per 1000 lbs | |
|---|---|---|
| | lbs | grams |
| (b) Ferrous Sulfate | 0.448 | 203.22 |
| (c) Vitamin Premix | 3.52 | 1597.0 |
|     Dextrose | 0.949 | 449.19 |
|     Taurine | 0.970 | 439.46 |
|     Inositol | | |
|     Zinc sulfate | 0.294 | 133.48 |
|     Niacinamide | 0.200 | 92.37 |
|     d-Calcium Pantothenate | 0.110 | 50.02 |
|     Ferrous Sulfate | 0.112 | 50.98 |
|     Thiamine (Vitamin B-1) | 0.030 | 14.14 |
|     Cupric sulfate | 0.060 | 27.63 |
|     Riboflavin (Vitamin B-2) | 0.014 | 6.25 |
|     Pyridoxine HCl (Vitamin B-6) | 0.013 | 5.74 |
|     Folic Acid | 0.0039 | 1.76 |
|     Manganese Sulfate | 0.003 | 1.24 |
|     Biotin | 0.001 | 0.505 |
|     Sodium Selenite | 0.0005 | 0.248 |
|     Cyanocobalamin (Vitamin B-12) | 0.000088 | 0.040 |
| (d) Manganese Sulfate | 0.0163 | 7.40 |
| (e) Choline Chloride | 2.06 | 934.00 |
| (f) L-carnitine | 0.310 | 140.61 |
| ASCORBIC ACID SOLUTION | | |
| (a) Potassium Hydroxide | 2.04 | 925.00 |
| (b) Ascorbic Acid | 2.95 | 1338.00 |
| OIL MIXTURE | | |
| (a) Hydrogenated Coconut Oil | 122.56 | 55,592.0 |
| (b) Palm Oil | 137.88 | 62,541.0 |
| (c) Soy oil | 45.96 | 20,847.0 |
| (d) Oil Soluble Vitamin Premix | 0.465 | 211.09 |
|     Refined Coconut Oil | 0.238 | 103.12 |
|     Vitamin A palmitate | 0.017 | 7.72 |
|     Vitamin D3 | 0.0001 | 0.053 |
|     Alpha-tocopherylacetate (Vitamin E) | 0.209 | 94.99 |
|     Phylloquinone (Vitamin K) | 0.00079 | 0.359 |
| (e) Emulsifier | 18.90 | 8,573.00 |
| (f) Ascorbyl palmitate | 0.252 | 114.30 |
| (g) Beta-carotene | 0.0126 | 5.72 |
| 5. CARIBOHYDRATE/MINERAL SLURRY | | |
| (a) Sodium Citrate | 8.46 | 3,837.00 |
| (b) Potassium Citrate | 5.93 | 2,690.00 |
| (c) Potassium Iodide | 0.0017 | 0.75 |
| (d) Magnesium Chloride | 5.64 | 2,558.00 |
| (e) Potassium Phosphate dibasic | 13.16 | 5,969.00 |
| (f) Calcium Carbonate | 2.27 | 1,030.00 |
| (g) Micronized Tricalcium Phosphate | 19.77 | 8,967.00 |
| (h) Corn Syrup Malto-Dextrins | 632.16 | 286,741.00 |

[1] Vitamin premix quantities listed above represent minimum values.

It is obvious to those skilled in the art, that the exact mass of each component given above in Table 1, can be varied slightly depending on the specifications of the starting materials used in the production of this material. However such variation in the composition of the Premix Base is restricted and limited within each class of compounds (i.e. nutrients, vitamins, minerals, carnitine and taurine). Examples of the range of values determined during manufacturing trials are indicated below in Table 2.

TABLE 2

Acceptable Component Range Limitations on the Premix Base.

| | Mass per 1000 grams of Powder | |
|---|---|---|
| | Minimum | Maximum |
| (a) Nutrients | | |
| Nitrogen (grams) | 0.0 | 0.65 |
| Fat (grams) | 310.0 | 320.0 |
| Carbohydrates (grams) | 600.0 | — |
| Water (grams) | 0.0 | 30.0 |
| Linoleic Acid (grams) | 27.0 | — |
| (b) Vitamins | | |
| Vitamin A (grams) | 0.006006 | 0.01487 |
| Vitamin D (grams) | 0.000116 | 0.000134 |
| Vitamin E (grams) | 0.1409 | 0.1745 |
| Vitamin K (grams) | 0.0007900 | 0.00126 |
| Vitamin B-1 (grams) | 0.025 | 0.042 |
| Vitamin B-2 (grams) | 0.0124 | 0.0191 |
| Vitamin B-6 (grams) | 0.0104 | 0.0133 |
| Vitamin B-12 (grams) | 0.0000650 | 0.000130 |
| Niacin (grams) | 0.1500 | 0.270 |
| Folic Acid (grams) | 0.003000 | 0.006000 |
| Pantothenic Acid (gram) | 0.0900 | 0.1400 |
| Biotin (grams) | 0.0009000 | 0.0016000 |
| Vitamin C (grams) | 1.8000 | 2.7000 |
| Choline (grams) | 1.5000 | 2.0000 |
| Inositol (grams) | 0.6800 | 0.9000 |
| (c) Minerals | | |
| Calcium (grams) | 7.50 | 9.75 |
| Phosphorous (grams) | 5.25 | 6.50 |
| Ca/P ratio | 1.15 | 1.90 |
| Magnesium (grams) | 0.630 | 1.000 |
| Iron (grams) | 0.119 | 0.140 |
| Zinc (grams) | 0.110 | 0.143 |
| Manganese (grams) | 0.0062 | 0.0084 |
| Copper (grams) | 0.0145 | 0.0190 |
| Iodine (grams) | 0.00125 | 0.00270 |
| Selenium (grams) | 0.000250 | 0.000400 |
| Sodium (grams) | 2.5000 | 2.8000 |
| Potassium (grams) | 8.7500 | 9.4000 |
| Chloride (grams) | 3.5000 | 4.000 |
| (d) Other | | |
| Taurine (grams) | 0.950 | 1.170 |
| Carnitine (grams) | 0.250 | 0.380 |

Described below are the specific details of each of the steps involved in the production of the powder Premix Base. These steps were outlined above.

1. Preparation of Stock Solutions:

An 8% total solids solution of water soluble vitamins was prepared by first heating the appropriate amount of water to a temperature of 43.3°–65.6° C. (110°–150° F.). Potassium citrate followed by ferrous sulfate were then added to the heated water and the mixture agitated until a clear green solution resulted. Then the water soluble vitamin/taurine/trace element premix, manganese sulfate, choline chloride and L-carnitine were added. This solution was moderately agitated and maintained at 43.3°–54.4° C. (110° to 130° F.) until required.

An ascorbic acid solution was prepared by combining the appropriate amount of room temperature ingredient water, 45% potassium hydroxide and ascorbic acid to make a solution containing 20% total solids. The pH range of the solution is 6.0–10.0, and was maintained thereat with low agitation until needed.

An oil blend was prepared by combining the soy, hydrogenated coconut and palm oils in a blend tank and heating the blend to a temperature of about 71.1°–76.7° C. (160° to 170° F.) with agitation. Next the oil soluble vitamin premix, containing vitamins A, D, E and K, was added to the oil blend. Then the specified amount of emulsifier (diacetyl tartaric acid esters of mono- and diglyceride) was completely dispersed in the heated oil blend. The antioxidant ingredients (ascorbyl palmirate and beta carotene) were then added. The resultant oil blend was maintained at a temperature of about 62.8°–68.3° C.(145°–155° F.) until combined with the carbohydrate-mineral slurry. While this illustrative example describes the use of palm, coconut and soy oils, as indicated previously, other oils may also be employed in the formation of this oil blend.

A carbohydrate and mineral slurry was prepared by placing the appropriate amount of water to make a slurry containing 40% total solids into a suitable tank and heating the water to a temperature of about 76.7°–82.2° C. (170° to 180° F.). Then the following mineral materials were added individually with high speed agitation to the heated water. Each mineral must be completely dissolved before addition of the next mineral. The sequence of mineral addition was: sodium citrate, potassium citrate, potassium iodide, magnesium chloride, potassium phosphate dibasic, calcium carbonate., and micronized tricalcium phosphate. While maintaining moderate agitation, the carbohydrate source (hydrolyzed corn syrup malto-dextrin) was added. The carbohydrate-mineral slurry was maintained at a temperature of 73.9°–76.7° C.(145° to 155° F.) with agitation for thirty minutes to ensure complete dissolution of the maltodextrins.

2. Combination of Stock Solutions.

The oil blend and carbohydrate-mineral slurry were then combined with agitation to yield a blend having 50–60% solids, by weight. The solution pH of the blend was maintained in the 6.50–7.0 range. If an adjustment Of pH was required, potassium hydroxide or citric acid was used. The temperature of the blend was adjusted to, and maintained at, 68.3°–71.1° C.(155°–160° F.) while the blend was agitated for thirty minutes. The blend was then homogenized at 168.7–182.78/28.1–42.2 kG/cm$^2$(2400–2600/400–600 psig). The homogenized blend was then cooled to a temperature of about 1.1°–5.6° C.(34°–42° F.).

Finally the water soluble vitamin and ascorbic acid solutions were added, with moderate agitation, to the homogenized blend to yield the liquid Premix Base slurry.

3. Drying of the Liquid Premix Base Slurry.

The liquid Premix Base slurry was pumped into a crystallizer tank and dried using a Filtermat F-4000 belt dryer manufactured by Niro Hudson, Inc., Hudson, Wis. However, such equipment is standard and known to those skilled in the art and any comparable equipment could be used in the manner described herein.

Drying parameters were as follows:

| | |
|---|---|
| Feed Temp.: | 73.9–79.4° C. (165–175° F.) |
| Crystallizer Tank Agitation: | low except HIGH for 1.5 minutes every 15 minutes |
| Number of Nozzles: | 7 |
| Nozzle Swirls: | SE |
| Nozzle Diameter: | 0.1245 cm (0.049 inches) |
| Nozzle Pressure: | 98.42–112.48 Kg/cm$^2$ (1400–1600 psig) |
| Nozzle Configuration: | all 7 positions have SE.049 |
| Surge Tank Agitation: | On |
| Surge Tank Level: | 90% |
| Primary Inlet Burner Temp.: | 182.2–198.8° C. (360–390° F.) |
| Dutch Weave Inlet Burner Temp.: | 182.2–198.8° C. (360–390° F.) |
| Primary Inlet Fan Speed: | 70–80% |
| Phlenum #2 Outlet Temp.: | 85.0–96.0° C. (185–205° F.) |
| Secondary Burner Temp.: | Off |
| Belt Speed: | 152 cm/minute (60 inches/minute) |
| Mill Screen Size: | Small |
| Mill Speed: | 25–50% |

Thereafter the dried Premix Base powder was filled into and stored in polymer lined fibers drums (approximately 450 kG (100 pounds) per drum).

EXAMPLE 2

The Premix Base prepared in Example 1, in addition to being packaged for use on its own as a separate medical food, was also used as starting material to manufacture eight different infant/toddler nutrient products. This is achieved by dry blending a certain amount of the Premix Base with one of eight different specific amino acid mixtures using the procedure described below. The procedure as described was identical for all eight of the specific amino acid combinations disclosed herein.

First, any amino acid mixtures that exhibited lumps were milled (delumped) using a Fluid Air Mill manufactured by Fluid Air, Naperville, Ill. However such equipment is standard and known to those skilled in the art and any comparable equipment could be used in the manner described herein.

Next, the milled amino acid mixtures were admixed with the Premix Base by dry blending: The Premix Base was added to a Littleford FKM Series Mixer manufactured by Littleford Brothers, Inc., Florence, Ky. However such equipment is standard and known to those skilled in the art and any comparable equipment could be used in the manner described herein.

A 600 liter or 4200 liter capacity mixer was selected depending on batch size. Batch size is targeted at 60% of total mixer (blender) capacity. The mixer was jogged as necessary to evenly distribute the Premix Base. The amino acids were then added through a small screen. Blending time for the 600 liter mixer was typically 5 minutes. Blending time for the 4200 liter mixer was typically 20 minutes.

The resultant dry powder blend from the mixer was discharged into appropriate storage containers. Finally this dry powder blend, being a homogeneous mixture of the Premix Base and the added amino acids, was dispersed into cans each holding amass of approximately 350 grams of powder per can.

EXAMPLE 3

Each of the eight amino acid formulations, corresponding to the individual nutrient requirements of eight different metabolic disorders, are described in Table 3.

TABLE 3

Amino Acid Composition of Specific Infant/Toddler Medical Foods[1]

| Formulation: | B | C | D | E | F | G | H | I |
|---|---|---|---|---|---|---|---|---|
| Composition: | | | | | | | | |
| Premix Base | 802.4 | 811.4 | 883.5 | 805.2 | 795.2 | 796.6 | 808.4 | 797.4 |
| L-Alanine | 13.063 | 12.995 | — | 10.206 | 5.103 | 5.352 | 5.352 | 5.148 |
| L-Glutamic Acid | 12.496 | 12.746 | — | 12.500 | 12.500 | 12.50 | 12.746 | 12.496 |
| L-Proline | 8.165 | 9.185 | — | 7.348 | 7.348 | 8.2557;552 | | 7.348 |
| L-Aspartic Acid | 8.097 | 8.165 | — | 8.097 | 7.666 | 8.097 | 8.165 | 7.643 |
| L-Lysine Acetate | 7.198 | 7.167 | 8.001 | 7.198 | 7.198 | — | 7.167 | 7.198 |
| L-Leucine | 7.031 | — | 11.068 | — | 8.573 | 8.573 | 8.&73 | 8.573 |
| L-Arginine | 6.872 | 7.189 | — | 6.872 | 5.307 | 6.872 | 7.076 | 5.398 |
| L-Tyrosine | 4.536 | 4.536 | 4.491 | 4.536 | 4.536 | 4.536 | — | 7.643 |
| L-Ca=itine | 4.454 | 0.386 | 0.835 | 4.454 | — | 4.454 | — | — |
| L-Phenylalanine | 4.491 | 4.491 | 3.833 | 4.491 | 4.491 | 4.491 | — | — |
| L-Serine | 3.606 | 4.536 | — | 3.878 | 3.833 | 4.082 | 3.924 | 3.878 |
| glycine | 2.540 | 5.103 | — | 5.103 | 5.103 | 5.103 | S.103 | 5.103 |
| L-Histidine | 2.132 | 2.132 | 1.837 | 2.132 | 2.132 | 2.132 | 2.132 | 2.132 |
| L-Cystine-dihydrochloride | 2.985 | 1.007 | 1.982 | 1.007 | 2.985 | 1.007 | 2.985 | -1.007 |
| L-Tryptophan | 0.862 | 0.862 | 1.429 | 0.862 | 0.862 | — | 0.862 | 0.862 |
| L-Isoleucine | 0.612 | — | 6.532 | 2.177 | 5.511 | 5.511 | 5.511 | 5.511 |
| L-Threonine | 0.510 | 3.561 | 3.833 | 3.561 | 3.561 | 3.561 | 3.561 | 3.561 |
| L-Glutamine | — | — | — | — | — | — | — | 0.658 |
| L-Methionine | — | 1.520 | 1.724 | 1.520 | — | 1.520 | — | 1.520 |
| L-Valine | — | — | 7.303 | 2.449 | 6.214 | 6.214 | 6.214 | 6.214 |

[1]Mass of ingredients per 100-0 lbs -of dry powder mix:
Premix Base ™ weight given in Lbs; Amino acid mass given in Kilograms.

EXAMPLE 4

As mentioned previously, at this time it is believed that what is critical in the instant invention is the ability to prepare a non-protein containing dry powder Premix Base which has a high fat content in the range of 31–39%. The specific oils forming the fat source are less important than the ability to produce a protein-free powder Premix Base having a high fat content as disclosed in Example 1 in the instant invention.

In some instances it may be desirable to replace all or part of the palm or coconut oils used in Example 1 with an oil having a low melting point, that is the temperature above which the oil is a liquid rather than a solid. Oils which have a low melting temperature are known in the art as "liquid oils" whereas oils which have a high melting temperature are known in the art as "solid oils". The advantages of using the "liquid" oils include the ability to process the oil blend at relatively low temperatures whereas oil blends containing the "solid" oils require that the blend be substantially heated following storage under cooled conditions, in order to decrease the blend's viscosity so that is can be easily handled. Such considerations may be considerable economic implications, particularly when considering the energy requirements of processing the two different types of oil blends.

A non-limiting example of the advantageous use of the liquid oils in the high fat Premix Base disclosed in the instant invention, is described below. Example 1 discloses use of an oil blend comprised of 15% soy, 40% hydrogenated coconut and 45% palm oil in the preparation of the Premix Base. Processing disadvantages with this oil blend have been experienced when the total solid concentration exceeds 50%. These disadvantages occur following homogenization and cooling of the oil blend to 4.4° C. (40° F.). Under these conditions it was noted that the carbohydrate-mineral-oil slurry tended to gelatinize and had a viscosity of 350 centipoises when measured at a shear rate of 1 reciprocal second. In contrast, when replacing completely the palm oil content of Example 1 with high oleic safflower oil and an increased soy oil content, yielding an oil blend comprising of 20% soy, 40% coconut and 40% safflower oil, while keeping the rest of the formulation and process unchanged, resulting in an carbohydrate-mineral-oil slurry which did not gelatinize at 4.4° C. (40° F.) and which had a viscosity of only 150 centipoise at 1 reciprocal second. It is believed that this advantageous consequence occurs as a result of the lower melting temperature reciprocal second. It is believed that this advantageous consequence occurs as a result of the lower melting temperature of the more "liquid" safflower and soy oils as compared to palm oil (41.1° C. or 106° F.).

EXAMPLE 5

As mentioned previously, to those skilled in the art of this invention, it will be clear that the fat content of the Premix Base instead of being described on the basis of individual oil name could also be described in terms of fatty acid compositions, wherein said fatty acids are themselves constituents of the individual oils, and wherein said fatty acid components are described on the basis of carbon chain length of and position of the double bonds (if any) present in the molecule, and wherein the chain length considered ranges from two (C2) to twenty (C20) carbon atoms.

In the preferred embodiment of the instant invention, said fat comprises (a) at least one fat selected from the group consisting of palm oil and safflower oil, (b) coconut oil, and (c) soy oil, and wherein the ratio of palm(safflower):coconut:soy oils is in the range of 9:8:3 to 3:8:9 parts by weight. Table 4 shows the fatty acid composition of the Premix Base as described above. This is simply an alternative method of characterizing the Premix Base wherein instead of characterizing the composition by oil name and content, said characterization of the same oil blend is made on the basis of fatty acid composition. Also given for comparison are some fatty acid compositions of alternative oil compositions.

TABLE 4

Fatty Acid Composition of Selected Premix Formulations

| Type of Fatty Acid | | | | Composition of Selected Oil Compositions (Weight Ratio as indicated) | | | | | | Range in Fatty Acid Composition as a % of Total Fat of various of Oil Blends | |
|---|---|---|---|---|---|---|---|---|---|---|---|
| Scientific name | Common name | Carbon chain length | Double Bonds | Palm:Hyd Coconut:Soy Oil Ratio: 9:8:3 | Palm:Hyd. Coconut:Soy 3:8:9 | Palm:Hyd. Coconut:Soy 4.5:8:7.5 | HO Saf-flower:Reg. Coconut:Soy 9:8:3 | Reg. Saf-flower:Reg. Coconut:Soy 9:8:3 | Safflower:Reg. Coconut:Soy 9:8:3 | Reg. Saf-flower:Reg. Coconut:Soy 9:8:3 | Minimum | Maximum |
| Hexanoic | Caproic | Six | None | 0.3 | 0.3 | 0.3 | 0.2 | 0.2 | 0.3 | 0.3 | 0.2 | 0.3 |
| Octanoic | Caprylic | Eight | None | 3.2 | 3.2 | 3.2 | 2.8 | 2.8 | 3.2 | 3.2 | 2.8 | 3.2 |
| Decanoic | Capric | Ten | None | 2.5 | 2.5 | 2.5 | 2.4 | 2.4 | 2.5 | 2.5 | 2.4 | 2.5 |
| Dodecanoic | Lauric | Twelve | None | 19.3 | 19.2 | 19.2 | 18.8 | 18.8 | 19.1 | 19.1 | 18.8 | 19.3 |
| Tetradecanoic | Myristic | Fourteen | None | 7.8 | 7.4 | 7.5 | 7.5 | 7.5 | 7.3 | 7.3 | 7.3 | 7.8 |
| Hexadecanoic | Palmitic | Sixteen | None | 24.9 | 14.9 | 17.4 | 6.9 | 8.3 | 6.8 | 8.3 | 6.8 | 24.9 |
| Octadecanoic | Stearic | Eighteen | None | 6.3 | 6.4 | 6.4 | 4.1 | 2.8 | 7.0 | 5.7 | 2.8 | 7.0 |
| 9-Octadecanoic | Oleic | " | One | 21.4 | 16.5 | 17.7 | 42.9 | 11.6 | 40.2 | 9.0 | 9.0 | 42.9 |
| 9,12-Octadecanoic | Linoleic | " | Two | 12.3 | 25.6 | 22.3 | 12.1 | 43.8 | 11.3 | 43.0 | 11.3 | 43.9 |
| 9,11,13-Octadecanoic | Linolenic | " | Three | 1.1 | 3.4 | 2.9 | 1.2 | 1.4 | 1.2 | 1.3 | 1.1 | 3.4 |
| Eicosanoic | Arachidic | Twenty | None | 0.23 | 0.2 | 0.2 | 0.27 | 0.22 | 0.23 | 0.18 | 0.2 | 0.3 |
| Docosanoic | Behenic | Twenty-two | None | 0.05 | 0.14 | 0.11 | 0.59 | 0.14 | 0.59 | 0.14 | 0.1 | 0.6 |

Each of the eight medical foods is defined individually by its specific amino acid composition and total energy content determined by the fat and carbohydrate content as disclosed in Table 3. In addition, unmodified the protein-free, fat-carbohydrate-vitamin-mineral rich Premix Base can be used as a medical food for infants and toddlers who need extra calories and protein restriction in their diets. These compositions together with the specific disease condition for which the medical food was developed are indicated below. The unmodified Premix Base is referred to as Formulation A.

| Formulation: | Intended for Nutritional Support of: |
| --- | --- |
| Formulation A: | Hypermetabolic states; Requirement for modified protein or amino acid intake; modifed energy, vitamin and mineral intake; |
| Formulation B: | Propionic acidemia & methylmalonic acidemia; |
| Formulation C: | Maple Syrup Urine Disease; |
| Formulation D: | Urea Cycle Disorders & Gyrate Atrophy; |
| Formulation E: | Isovaleric Acidemia & Other Leucine Catabolic Disorders |
| Formulation F: | Homocystinuria, B-6 Non-responsive, and Hypermethioninemia |
| Formulation G: | Glutaric Aciduria Type 1; |
| Formulation H: | Tyrosinemia Type 1 |
| Formulation I: | Phenylketonuria & Hyperphenylalaninemia |

In addition, to the carnitine content of the premix composition, certain of these medical foods are further fortified with the amino acid carnitine as indicated in Table 3.

Following sealing and labeling, the cans were then ready for commercial distribution. Upon purchase or receipt of the specific metabolic food, the prescribed amount of product is mixed with the prescribed amount of infant formula and water to yield a known volume having a prescribed metabolic food concentration. No general formulation recipe can be given since ingestion of each metabolic food is individual or patient specific.

INDUSTRIAL APPLICABILITY

This invention overcomes numerous problems associated with prior art medical foods. It is quite apparent that the employment of the generic premix powder base will substantially enhance ease of preparation and cost-effectiveness of production of medical foods according to the present invention and hence accelerate commercial production of these medical foods for the nutritional support of certain metabolic disorders.

The embodiments of the present invention may, of course be carried out in other specific ways than those set forth herein without departing from the spirit and essential characteristics of the invention. The present embodiments are, therefore, to be considered in all respects as illustrative and not restrictive and all changes coming within the meaning and of equivalents.

We claim:

1. A method of providing enteral nutritional support for an infant/toddler having an inherited metabolic disease selected from the group consisting of tyrosinemia, alcaptonurta, isovaleric acidemia, homocystinuria, urea cycle disorders, or an organic acid metabolic disorder comprising enterally feeding the infant/toddler in need of such nutritional support an effective amount of a composition having utility for the nutritional support of infants and toddlers having inherited diseases of metabolism, the composition comprising a physical admixture of:

(a) a premix base which is a composition of matter that is essentially free of protein and amino acids and consists essentially of fats comprising 30 to 40% by dry weight of the premix base, carbohydrates comprising 60 to 70% by dry weight of the premix base, minerals comprising 0.1 to 8% by dry weight of the premix base, vitamins comprising 0.1 to 1.0% of the premix base, trace elements, carnitine, routine and antioxidants; and (b) a blend of synthetic α-amino acids that comprises up to 18 different synthetic α-amino acids selected from the group consisting of L-alanine, L-arginine, L-aspartic acid, L-cystine, L-glutamic acid, L-glutamine, glycine, L-histidine, L-isoleucine, L-leucine, L-lysine, L-methionine, L-proline, L-phenylalanine, L-serine, L-threonine, L-tryptophan, L-tyrosine and L-valine, the composition being in powdered form with the premix base comprising about 75 to 90% by dry weight of the composition and the blend of synthetic α-amino acids comprising about 9 to 25% by dry weight of the composition, and the composition being free of intact protein.

2. The method of claim 1, wherein the organic acid metabolic disorder is selected from the group consisting of propionic acidemia, methylmalonic acidemia and glutaric aciduria Type 1.

* * * * *